US00PP34699P2

(12) United States Plant Patent
Hochberg

(10) Patent No.: US PP34,699 P2
(45) Date of Patent: Nov. 1, 2022

(54) CAMPSIS PLANT NAMED 'HOCH128'

(50) Latin Name: *Campsis tagliabuana*
Varietal Denomination: HOCH128

(71) Applicant: Hochberg Ornamental Export Plants Ltd., Moshav Bitzaron (IL)

(72) Inventor: Omer Hochberg, Moshav Bitzaron (IL)

( * ) Notice: Subject to any disclaimer, the term of this patent is extended or adjusted under 35 U.S.C. 154(b) by 0 days.

(21) Appl. No.: 17/668,666

(22) Filed: Feb. 10, 2022

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

(56) References Cited

PUBLICATIONS

CPVO Application Consultation website (retrieved Mar. 7, 2022) (Year: 2022).*

* cited by examiner

*Primary Examiner* — Keith O. Robinson
(74) *Attorney, Agent, or Firm* — Cassandra Bright

(57) ABSTRACT

A new and distinct cultivar of *Campsis* plant named 'HOCH128' is disclosed, characterized by red flowers, and long internodes. Plants are vining produce new flowers and flower buds throughout Summer. The new variety is a *Campsis*, normally used for outdoor ornamental purposes.

2 Drawing Sheets

Figure 1:
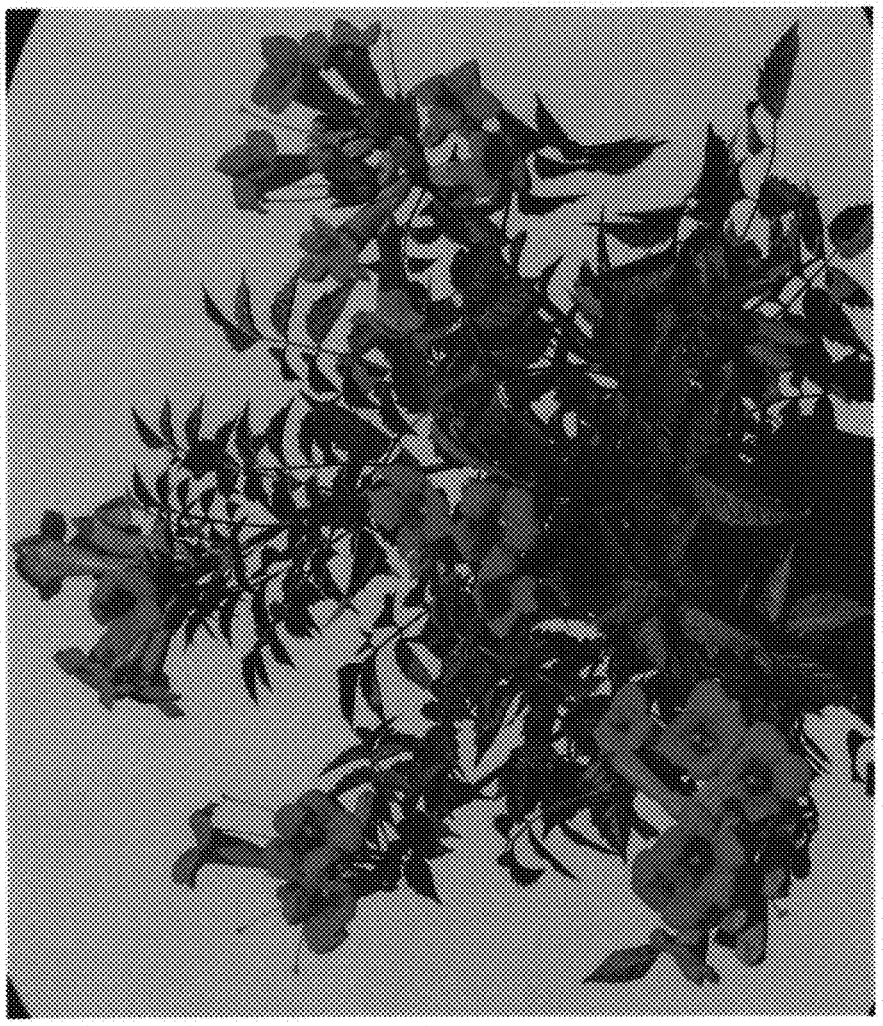

Latin name of the genus and species: *Campsis tagliabuana.*

Variety denomination: 'HOCH128'.

BACKGROUND OF THE INVENTION

The new *Campsis* cultivar is a product of a planned breeding program conducted by the inventor, in Moshav Bitzaron, Israel. The objective of the breeding program was to develop new *Campsis* plants for ornamental purposes. The cross resulting in this new variety was made during September of 2012.

The seed parent is an unnamed, unpatented proprietary variety of *Campsis tagliabuana*. The pollen parent is a different unnamed, unpatented proprietary variety of *Campsis tagliabuana*. The new variety was selected in July of 2014 by the inventor in a group of seedlings resulting from the 2012 crossing, in a nursery in Moshav Bitzaron, Israel.

Asexual reproduction of the new cultivar was performed by grafted softwood cuttings. This was first performed at the same nursery in Moshav Bitzaron, Israel during January of 2015, and has shown that the unique features of this cultivar are stable and reproduced true to type in multiple successive generations.

SUMMARY OF THE INVENTION

The cultivar 'HOCH128' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HOCH128' These characteristics in combination distinguish 'HOCH128' as a new and distinct *Campsis* cultivar:

1. Distinctive red flower color.
2. Long internodes.

PARENT COMPARISON

Plants of the new cultivar 'HOCH128' are similar to plants of the seed parent in most horticultural characteristics; however, plants of the new cultivar 'HOCH128' differ in the following;

1. The new variety has smaller flowers than the seed parent.
2. Flowers of the new variety are more open at the ends, less cylindrical than flowers of the seed parent.
3. Plants of the new variety are not as compact as plants of the seed parent.

Plants of the new cultivar 'HOCH128' are similar to plants of the pollen parent in most horticultural characteristics; however, plants of the new cultivar 'HOCH128' differ in the following;

1. The new variety has red flowers, while the pollen parent has yellow flowers.
2. Plants of the new variety do not grow as vigorously as plants of the pollen parent.

COMMERCIAL COMPARISON

Plants of the new cultivar 'HOCH128' are comparable to the commercial variety *Campsis* 'Kudian', U.S. Plant Pat. No. 13,139. The two *Campsis* varieties are similar in most horticultural characteristics; however, the new variety 'HOCH128' differs in the following;

1. The new variety has red flowers; this comparator has orange blooms.

2. Plants of the new variety are more compact than plants of this comparator.

Plants of the new cultivar 'HOCH128' are comparable to the commercial variety *Campsis* 'Takarazuka Fresa', U.S. Plant Pat. No. 23,917. The two *Campsis* varieties are similar in most horticultural characteristics; however, the new variety 'HOCH128' differs in the following;

1. The new variety has longer flowers than flowers of this comparator.
2. Plants of the new variety have longer internodes than plants of this comparator, producing overall taller plants.
3. Plants of the new variety are not as compact as plants of this comparator.

BRIEF DESCRIPTION OF THE PHOTOGRAPHS

Figure 2:
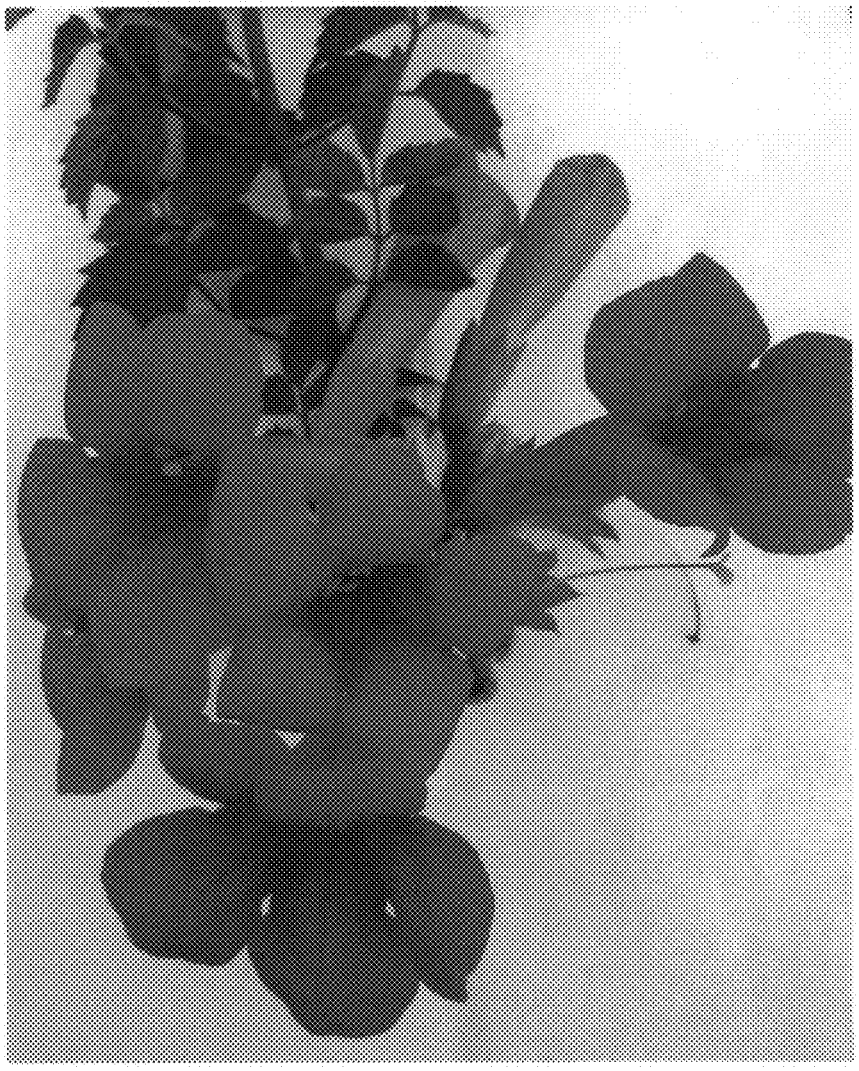

The accompanying photograph in FIG. 1 illustrates a typical flowering plant of 'HOCH128' grown outdoors in Moshav Bitzaron, Israel at approximately 1 year of age. FIG. 2 illustrates a close-up view of flowers of the new variety. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'HOCH128' plants grown outdoors during 2021, in Visalia, Calif. The growing temperature ranged from approximately 18° C. to 38° C. during the day and from approximately 5° C. to 10° C. during the night. General light conditions are normal sunlight and numerical values represent averages of typical plant types.

Botanical classification: *Campsis tagliabuana* 'HOCH128'.

PROPAGATION

Type of propagation typically used: Softwood stem cuttings.

PLANT

Age of plant described: About 1.5 years old from a rooted cutting.
Container size: 2 gallon container.
Growth habit: Upright.
Plant spread: 35 cm.
Plant height: 65 cm.
Plant vigor: Moderate.
Length of primary stems: 50 to 70 cm on average.
Diameter of primary stems: 7 to 8 mm.
Quantity of primary stems: About 3 to 4.
Stem:
- *Color*.—New growth: Near RHS Green 143C. Old growth: Near RHS Yellow-Green 146B.
- *Shape*.—Round.
- *Strength*.—Good, flexible.
- *Texture*.—Very slightly pubescent on youngest growth, striated with age.

Internode length: Average range 10 to 16 cm.
Bark: Not observed.

FOLIAGE

Leaf:
- *Arrangement*.—Pinnately compound with 7 to 10 leaflets.
- *Average length*.—10 to 20 cm.
- *Average width*.—8 to 12 cm.
- *Leaflets*.—Arrangement: Odd pinnate. Length: Average range 2 to 8 cm. Width: Average range 1.5 to 3 cm. Shape of blade: Ovate-oblong or ovate. Apex: Acute. Base: Cuneate. Margin: Serrate. Aspect: Slightly concave from mid-rib, slightly reflexed back. Texture of top surface: Smooth. Matte. Texture of bottom surface: Smooth. Matte. Color: Young foliage upper side: Near RHS Green 143A. Young foliage under side: Near RHS Green 143B. Mature foliage upper side: Near RHS Green 137A. Mature foliage under side: Near RHS Green 137D. Venation: Type: Pinnate. Venation color upper side: Near RHS Yellow-Green N144B. Venation color under side: Near RHS Yellow-Green N144B.

Petiole:
- *Length*.—3 to 5 cm.
- *Width*.—2 mm.
- *Color*.—Upper side: RHS Yellow-Green 144A. Under side: RHS Yellow-Green 144B.
- *Texture*.—Upper side: Lightly pubescent. Under side: Lightly pubescent.

Petiolules:
- *Length*.—5 to 9 mm.
- *Width*.—2 mm.
- *Color*.—Upper side: RHS Yellow-Green N144B. Under side: RHS Yellow-Green N144D.
- *Texture*.—Upper side: Glabrous. Under side: Glabrous.

Rachis:
- *Length*.—5 to 10 cm.
- *Width*.—3 mm.
- *Color*.—Upper side: RHS Yellow-Green 144A. Under side: RHS Yellow-Green 144B.
- *Texture*.—Upper side: Glabrous. Under side: Glabrous.

FLOWER

Natural flowering season: Late Spring through Fall. Begins flowering mid-May in California.
Inflorescence form: Terminal cluster.
Flowers per inflorescence: About 7 to 12 flowers and buds.
Inflorescence size:
- *Width*.—Average range 18 to 20 cm.
- *Length*.—Average range 18 to 20 cm.

Individual flowers:
- *Shape*.—Campanulate.
- *Habit*.—Whorled outward.
- *Diameter*.—6.2 cm.
- *Length*.—10 cm to 11 cm.
- *Persistence*.—Self-cleaning.
- *Fragrance*.—None.

Petals:
- *Arrangement*.—Rotate at end of tube.
- *Number*.—5.
- *Shape*.—Overall irregular orbicular
- *Aspect*.—Reflexed back.
- *Margin*.—Entire.
- *Tip shape*.—Broad rounded to truncate.

*Base shape*.—Rounded.
*Length*.—2.5 cm.
*Width*.—2.5 cm.
*Appearance*.—Matte.
*Texture*.—Upper: Glabrous. Lower: Glabrous.
*Color*.—When opening: Upper surface: Near RHS Red 42A. Under surface: Near RHS Red 40B. Fully opened: Upper surface: Near RHS Red 44A lightly flushed Red 40C. Veins near 46A. Under surface: Near RHS Red 44B flushed Red 40B. Veins near Red 46B. Throat color: Red 44A with veins near Red 46A.

Corolla tube:
*Length*.—Average 9 cm.
*Diameter*.—2.5 cm.
*Color*.—Interior: Near RHS Red 44A flushed Red 40B, veins near 46A. Exterior: Near RHS Red 43A flushed Red 40B, veins near 46B.

Bud:
*Shape*.—Tapered elliptic.
*Length*.—3 cm.
*Diameter*.—1 cm.
*Color*.—Near RHS Orange-Red N30B, flushed Red 45B. Veins near Red 45C.
*Appearance*.—Matte.

Calyx:
*Shape*.—Campanulate.
*Length*.—3.0 cm.
*Diameter*.—1.5 cm.

Sepals:
*Appearance*.—Matte all surfaces.
*Arrangement*.—Rotate, fused from base to about 70% of length.
*Unfused sepal section*.—Shape: Deltate. Tip shape: Acute. Margin: Entire. Quantity per flower: 5. Length: 9 mm. Width: 5 mm. Margin: Entire. Texture: Inner: Smooth. Outer: Smooth. Color: Inner: Near RHS Yellow-Orange 14B flushed Orange 24A. Outer: Near RHS Orange N25D with strong overall flush Red 40C.

Peduncle:
*Length*.—Average range 1.5 to 2.5 cm.
*Diameter*.—4 mm.
*Texture*.—Glabrous.
*Color*.—Near RHS Yellow-Green 144C.
*Orientation*.—Upright and outward.
*Strength*.—Strong.

Pedicel:
*Length*.—5 to 7 mm.
*Diameter*.—2 mm.
*Angle*.—About 45 degrees from attachment.
*Strength*.—Moderate.
*Texture*.—Glabrous.
*Color*.—Near RHS Yellow-Green 144C.

REPRODUCTIVE ORGANS

Stamens:
*Number*.—4.
*Filament length*.—About 3.9 cm.
*Filament color*.—Near RHS Yellow-Orange 20C.

Anthers:
*Shape*.—Flattened elliptic.
*Length*.—3 mm.
*Color*.—Near RHS Yellow-Orange 20B.
*Pollen*.—Moderate, colored near Yellow-Orange 18D.

Pistil:
*Number*.—1.
*Length*.—3.2 cm.
*Style color*.—Near RHS Yellow-Orange 22B.

Stigma:
*Shape*.—Flattened petaloideo, bifurcate.
*Color*.—Near RHS Yellow-Orange 22A.
*Ovary color*.—Near RHS Yellow 2D.

OTHER CHARACTERISTICS

Fruits and seeds: Not observed to date.
Disease/pest resistance: Neither resistance nor susceptibility to normal diseases and pests of *Campsis* observed.
Temperature range: USDA Zones 5 through 9.

What is claimed is:

1. A new and distinct cultivar of *Campsis* plant named 'HOCH128' as herein illustrated and described.

* * * * *